United States Patent [19]
Serkes et al.

[11] Patent Number: 5,151,366
[45] Date of Patent: Sep. 29, 1992

[54] CELL CULTURE FLASK

[75] Inventors: Jonathan M. Serkes, Oak View; Richard C. St. Pierre, Thousand Oaks, both of Calif.

[73] Assignee: Invitro Scientific Products, Inc., Ventura, Calif.

[21] Appl. No.: 705,564

[22] Filed: May 24, 1991

[51] Int. Cl.$^5$ .................... C12M 3/04; C12M 1/24
[52] U.S. Cl. .................... 435/285; 435/284; 435/296; 435/310; 422/102
[58] Field of Search ............. 435/284, 285, 286, 297, 435/298, 299, 296, 310; 422/102; 215/1 C, 1 R; 220/670, 671, 672, 673, DIG. 12, DIG. 13, DIG. 14

[56] References Cited

U.S. PATENT DOCUMENTS

| | | | |
|---|---|---|---|
| D. 285,725 | 9/1986 | Franchere | D24/56 |
| 3,249,504 | 5/1966 | Cappel et al. | 435/240.3 |
| 3,532,605 | 10/1970 | Riera | 435/296 |
| 3,589,983 | 12/1968 | Holderith et al. | 435/296 |
| 3,701,717 | 10/1972 | Ingvorsen | 435/296 |
| 3,870,602 | 3/1975 | Froman et al. | 435/296 |
| 3,893,887 | 7/1975 | Smith et al. | 435/240.23 |
| 3,941,661 | 3/1976 | Noteboom | 435/285 |
| 4,121,976 | 10/1978 | Gleeson | 435/296 |
| 4,172,013 | 10/1979 | Skoda et al. | 435/285 |
| 4,242,459 | 12/1980 | Chick et al. | 435/283 |
| 4,317,886 | 3/1982 | Johnson et al. | 435/285 |
| 4,514,499 | 4/1985 | Noll | 435/284 |
| 4,657,867 | 4/1987 | Guhl et al. | 435/284 |
| 4,665,035 | 5/1987 | Tunac | 435/296 |
| 4,770,854 | 9/1988 | Lyman | 422/102 |
| 4,824,787 | 4/1989 | Serkes et al. | 435/285 |
| 4,829,004 | 5/1989 | Varani et al. | 435/296 |
| 4,912,048 | 3/1990 | Smith et al. | 435/296 |
| 4,912,058 | 3/1990 | Mussi et al. | 435/285 |
| 4,939,151 | 7/1990 | Bacehowski et al. | 435/284 |
| 4,962,033 | 10/1990 | Serkes et al. | 435/240.243 |
| 5,010,013 | 4/1991 | Serke et al. | 435/285 |

FOREIGN PATENT DOCUMENTS

| | | |
|---|---|---|
| 1191951 | 10/1959 | France . |
| 1413545 | 11/1964 | France . |
| 8604085 | 7/1986 | PCT Int'l Appl. . |

OTHER PUBLICATIONS

Medical Polymers and Plasma Technology, S. L. Kaplan, T. S. Dunn and P. W. Rose, PLASMA SCIENCE, Inc. Belmont, Calif., Oct., 1988, pp. 1-6.

Identifying and Correcting Common Cell Culture Growth and Attachment Problems, John A. Ryan, Cell Culture, Jan. 1989, pp. 8-16.

Surface Treatments and Cell Attachment, W. S. Ramsey, et al., Oct., 1981. In Vitro, vol. 20, No. 10, pp. 802-808.

*Primary Examiner*—Robert J. Warden
*Assistant Examiner*—William H. Beisner
*Attorney, Agent, or Firm*—Marvin E. Jacobs

[57] ABSTRACT

A laboratory flask for growing attachment dependent cell cultures in which the media immersed bottom surface is corrugated in a plurality of like sized regions to provide increased growing surface. The corrugated regions are separated by flat regions that allow visual inspection and also structurally reinforce the corrugation weakened flask. Alternatively, each pair of corrugations may have a flat area therebetween.

19 Claims, 2 Drawing Sheets

1

CELL CULTURE FLASK

TECHNICAL FIELD

This invention in the biotechnology field concerns improvements in the flasks within which cell cultures are cultivated. More specifically, a flask is described that has an enhanced surface area upon which to grow cells without compromising necessary structural characteristics.

1. Background of the Invention

It is useful and desirable to grow as many cells as possible in a controlled environment for research purposes or to obtain the cell by-products therefrom. This is routinely done in laboratory flasks into which some cells are introduced. The cells attach to and grow on the bottom wall of the flask, immersed in a suitable sustaining media. The flask is kept in an incubator to maintain it at the proper temperature.

Typically, many flasks are stacked together in the incubator and a number of cultures are simultaneously grown. Small variations in the growth medium, temperature, and cell viability have a pronounced effect on the progress of the cultures. Consequently, repeated microscopic visual inspections are needed to monitor the growth of the cells. These inspections involve carefully removing a flask from the incubator, keeping it level, and placing it on an inverted microscope. The microscope can be focused on the cell layer inside the transparent bottom wall of the flask so as to permit a detailed examination.

Attachment cells, the target culture of the present invention, need a suitable surface which they can attach to before they can multiply and create a layer over the full surface area available. When the surface is fully occupied, a condition called confluency, further growth is blocked. Thus, the production of cells or cell by-products is limited. Using more flasks has the disadvantage of requiring more handling, more microscope examinations, more risk to the flask contents in the form of contamination or physical damage, and more expense. If each flask could have a greater growing surface area, productivity would clearly be improved. But any change of the flat horizontal growing surface has been regarded as unworkable for a number of reasons.

Firstly, if the growing surface is not flat, it is not possible to focus the inverted microscope on the very thin mono-layer of cells thereon. Secondly, if the surface is not flat, particularly sensitive cells may not grow uphill on the non-horizontal surfaces. Furthermore, the repeated thermal changes resulting from moving the flasks in and out of the incubator for inspections tend to warp and distort the growing surface which disturbs the cells and complicates the task of focusing the microscope. This problem is exacerbated if the surface is not flat. Still another problem is encountered when the time comes to remove the contents of the flask. Non-flat growing surfaces trap the contents in the convolutions making access and removal laborious and difficult. The present invention strives to overcome all of the above disadvantages.

2. Statement of the Prior Art

A typical example of the prior art is shown in U.S. Pat. No. 4,770,854 to Lyman which discloses a rectangular culture flask having a neck shaped and angled to optimize access to the interior. The bottom wall 16, where growth normally takes place, is flat in accordance with the prevailing wisdom of the prior art.

A variation on the above theme may be seen in United States Patent Des. 285,725 to Franchere which has the neck located in the corner but still retains the flat bottom needed for optical examination.

U.S. Pat. No. 4,824,787 to Serkes et al. shows not a flask, but a cell culture container in a related art. Serkes et al. describes a roller bottle for the growing of cells in more of a high production environment. Cells that have been developed or selected to be more hardy are introduced into a roller bottle that revolves continuously during incubation keeping the full interior wall of the bottle periodically bathed with nutrient solution. These hardier cells can withstand turbulence, movement, and general disruption. Thus, the walls can be corrugated to increase the growing area and yield. The cells can still attach to these corrugated walls since the cells are generally more rugged. The transfer of these corrugations, however, to the research type rectangular flask has been thought to be a poor idea since these flasks remain still and horizontal. Hence, corrugations make practically all of the growing surface non-horizontal all of the time, impeding attachment and growth. This disadvantage is made worse by the more finicky nature of research cells which include, for example, primary cells taken directly from animals for study and neuron type cells that are particularly hard to induce to grow. This invention discloses a flask design with increased growing surface for the more fragile cells as well.

SUMMARY OF THE INVENTION

Briefly, the flask of the present invention incorporates a growing surface that blends a balanced combination of corrugated areas, to increase the surface area upon which cells may grow, and flat areas intermixed with the corrugated areas to permit microscopic inspection of the cell layer. The flat areas are dispersed in such a way as to insure that any given growing area is proximate to an inspection area so that a comprehensive and representative examination is possible despite the fact that the majority of the flask growing surface is not accessible to the microscope. In addition, the flat areas serve to maintain structural integrity across the whole of the growing surface. Without the flat areas, the corrugations introduced into the flat flask wall would weaken it excessively allowing the flask to expand when warmed in the incubator. Such expansion makes stacking in the incubator impossible and use of the microscope impossible. Another improvement stems from orienting the corrugations with their fold lines pointing toward the flask opening to make removal of the contents easier and more complete.

The details of this invention, along with additional benefits and advantages, are explained hereinafter and with reference to the drawings.

DETAILED DESCRIPTION OF THE INVENTION

Figure 1:
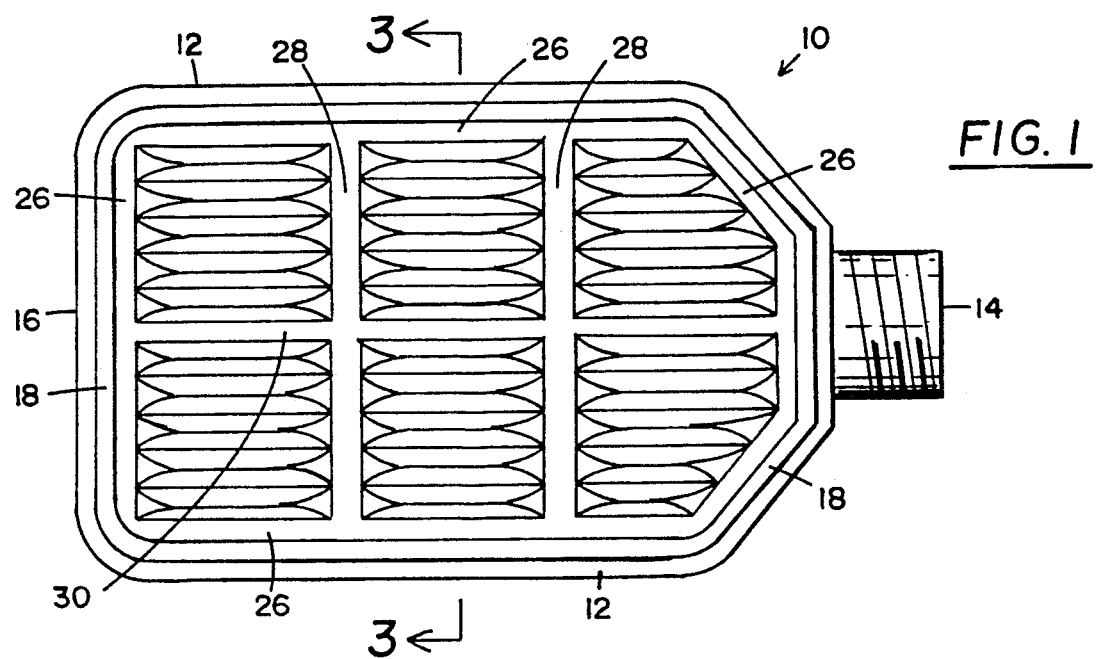
FIG. 1 is an elevational view of the flask of the present invention as seen from the bottom or growing surface side showing the fluted or corrugated areas and the intermixed flat areas.

In FIG. 1, the flask 10 of the present invention is shown from the bottom side which is the side upon which cells are normally cultured. The flask includes edge walls 12, a threaded opening 14 adapted to receive a conventional screw cap, and an end wall 16 opposite opening 14. Flask 10 is more or less rectangular to facilitate efficient and compact stacking in the incubator. To avoid any chance of leaks, flask 10 is preferably blow molded from a single piece of transparent plastic. A good choice for this plastic is polyethylene terephthalate with a glycol additive, an amorphous thermoplastic that not only has good forming properties but also has been found to have acceptable cell attachment and release characteristics. Also, this plastic can withstand sterilization by gamma radiation without physical and chemical degradation. This plastic is commercially available from Eastman Chemical under the trademark Kodar 6763.

Figure 2:
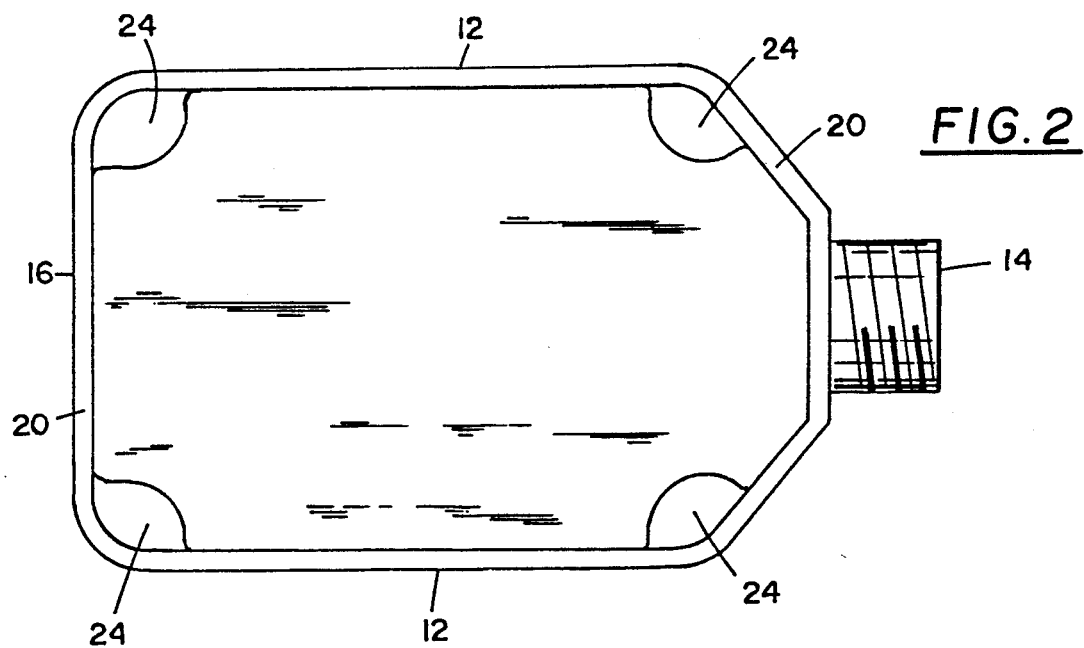
FIG. 2 is a view of the opposite side of the flask from that shown in FIG. 1 showing the top surface and the stacking risers thereon and the retaining rim.
Figure 3:
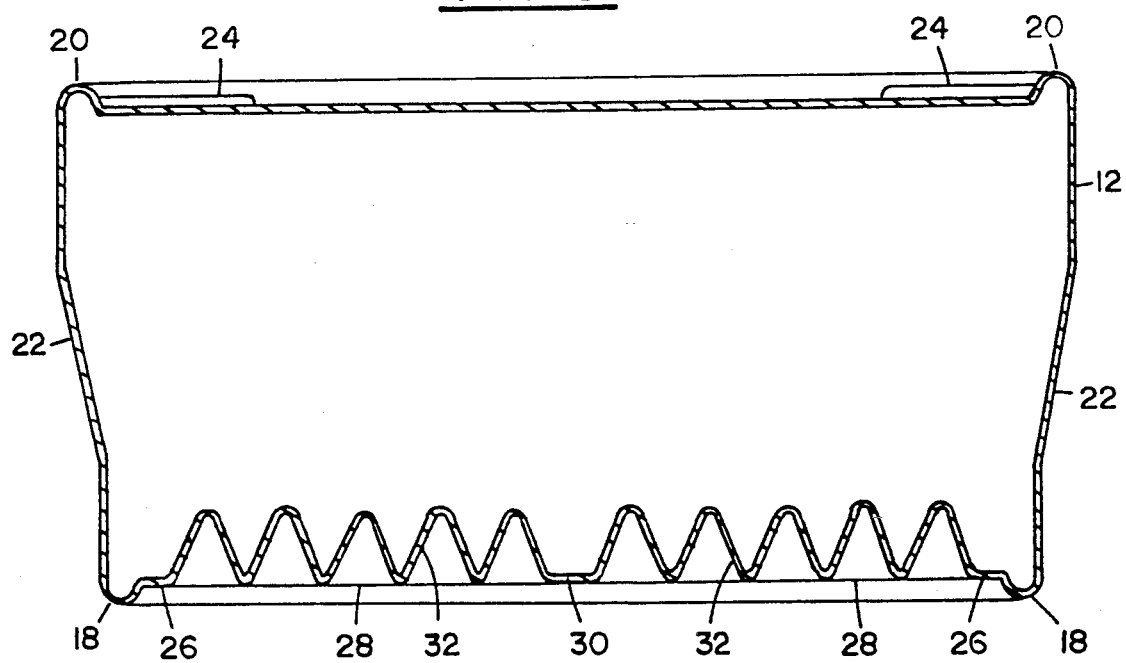
FIG. 3 is a sectional view taken on line 3—3 in FIG. 1 that further illustrates the important features of the flask.

The bottom growth surface of the flask is surrounded by a peripheral raised rim or bead 18 that is perhaps easier to see in the cross section of FIG. 3. The opposite or top side of the flask, as shown in FIG. 2, also has a peripheral rim 20 that is slightly larger than rim 18. Edge walls 12 slant out as shown by portions 22 in FIG. 3 so that the flasks can be nested or stacked with rim 18 coming to rest just inside rim 20 and on a group of four platforms or risers 24.

Referring to FIGS. 1 and 3, it may be seen that the bottom wall of flask 10 has a mixture of flat and corrugated areas. Six approximately square areas of corrugations are defined by flat areas around and between the square areas. Since the flask shown is about 3 by 4 inches, the square areas are about an inch square. Larger flasks would have more square areas so as to keep the square areas about the same size. The corrugations increase the growing surface area while the flat areas provide an optically flat transparent wall where a microscope can be positioned and focused to examine the cells inside the flask. The flat areas have other functions as well. A peripheral border flat zone 26 is formed just inside rim 18. This border flat zone laterally stiffens the surface at the edges and keeps the rim 18 straight to insure proper stacking of the flasks. Thermal stresses might otherwise distort the flask rim as it is moved in and out of the incubator.

A pair of flat cross band areas 28 are formed that extend from the border flat on one side to the border flat on the opposite side. Cross bands 28 comprise tension members that prevent the flask from expanding outward in response to internal pressure in the flask. In use, the flask is sealed and warmed in the incubator. Warming raises the pressure inside the flask, typically about 1 psi. The flask walls are very thin and the folds weaken it considerably in the direction perpendicular to the folds. Hence, internal pressure in the flask easily bows the bottom and edge walls outward. This bowing is resisted by tension bands 28. Without restraint, the bowing could prevent stacking and distort the flat areas enough to make examination by microscope impossible.

A third flat area 30 is formed from the border flat near opening 14, generally down the center of the flask bottom, to the border area near end 16. The combination of flat areas 26, 28, and 30 divide the flask bottom into six corrugated areas each filled with a series of folds 32 that significantly increase the surface area for cell attachment and growth. The surface area is about doubled with the fold shape shown in FIG. 3. Deeper folds would, of course, give even more area but tend to trap the contents in the deeper crevices. On larger flasks, additional flat areas would be needed to define more than six corrugated areas, keeping the corrugated area the proper size.

One of the strongest contributors to variations in cell growth are temperature gradients in the incubators. Most often, one sees a different progress at one end of the flask relative to the other end. Reducing the distance from one flat viewing area to the next lessens the probability of overlooking a variation in the effect of the temperature. The arrangement of flat viewing areas 26, 28, and 30 affords a balanced mixture of flat and corrugated areas that optimizes growing surface but still insures that any location on the bottom wall is only a short distance from a flat viewing area. Accordingly, the cells that may be microscopically examined are likely to comprise a representative sample of the condition of all cells in the flask.

Figure 4:
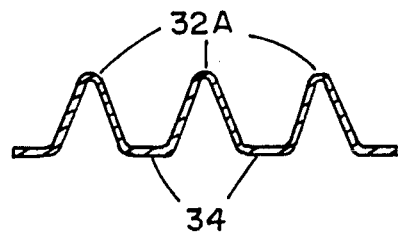
FIG. 4 is a sectional fragmentary view, similar to the bottom part of FIG. 3, showing another shape for the corrugated growing surface with flat areas between each pair of flutes.
Figure 5:
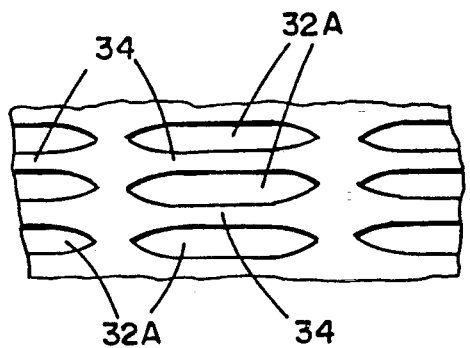
FIG. 5 is a fragmentary elevational view, similar to FIG. 1, showing the embodiment of FIG. 4 with additional flat areas between the flutes.

When cell cultures are more uneven in their growth rates, it may be desirable to provide even more viewing areas. In FIGS. 4 and 5, another embodiment of the invention is illustrated wherein flat viewing areas are introduced between each pair of individual corrugations. FIG. 4 is a section of the growth surface that may be used instead of the folds 32 shown in FIG. 3. Each pair of folds 32A has a flat viewing area 34 formed therebetween to provide an inspection zone proximate every fold. A portion of the resulting bottom growth surface is shown in FIG. 5. This embodiment of the invention provides a great increase in inspection area but, of course, some reduction in growing surface.

The folds in each corrugated area are oriented parallel to edge walls 12 so as to create grooves or channels that point toward and convey fluid to the opening 14 to make removal of cells or cell by-products easier. Channels oriented in a different direction would trap the valuable contents of the flask making removal very difficult. However, this necessary orientation causes the bottom wall to be susceptible to the bowing effect discussed previously. Hence, the tension strap function of flat areas 28 provides a synergistic benefit in addition to the primary function of providing a viewing location.

Widths, lengths, and spacings of the flat viewing areas are controlled, in part, by the flat area requirements of the microscope, the overall flask size, and the cell growth characteristics. Therefore, the particular arrangement of flat areas shown in the drawings is not critical. Numerous variations may be seen to fall within the scope and spirit of the invention. Limitation of the invention is solely determined by the appended claims and their equivalents.

We claim:

1. In a stackable, generally rectangular, cell culture flask having a top wall and a bottom wall connected to side walls and end walls, one of said end walls including a neck and closure, the improvement comprising:

said bottom wall comprising an extended surface area and having an interior surface capable of attachment and confluent growth of animal cells, said bottom wall containing a plurality of parallel, non-horizontal folds and at least one flat viewing panel disposed adjacent to said folds and said folds comprising a majority of the interior surface of said bottom wall whereby the surface area for cell growth of said bottom wall is significantly increased.

2. A cell culture flask according to claim 1 in which the folds have a longitudinal axis, the bottom wall contains a plurality of said flat viewing panels and a first portion of said flat viewing panels are disposed parallel to said longitudinal axis of the folds.

3. A cell culture flask according to claim 2 in which a second portion of said flat viewing panels are disposed transverse to the longitudinal axis of said folds.

4. A cell culture flask, according to claim 3, in which at least one of the axially disposed or transversely disposed flat panels extend completely across the bottom wall of the flask to form tension members that support the support wall.

5. A cell culture flask, according to claim 4, in which both the axially and transversely disposed flat panels extending completely across the bottom wall of the flask.

6. A cell culture flask according to claim 2 in which the flask has an axis parallel to said side walls and the longitudinal axis of said folds is disposed parallel to the axis of the flask.

7. A cell culture flask, according to claim 3, in which a plurality of parallel folds are disposed adjacent to each other to form at least one region.

8. A cell culture flask according to claim 7, in which said flat panels completely surround each of said regions of folds.

9. A cell culture flask, according to claim 4, in which one of said flat panels is disposed along the perimeter of the bottom wall.

10. A cell culture flask, according to claim 9, in which the bottom wall contains at least 2 transverse, flat panels.

11. A cell culture flask, according to claim 2, in which one of said flat panels is disposed adjacent each fold.

12. A cell culture flask, according to claim 2, in which each fold has a lowermost edge and substantially all of said edges are disposed in a common plane.

13. A cell culture flask, according to claim 2, in which said bottom wall has at least about twice the surface area of a comparably sized bottom wall with a flat interior surface.

14. In a stackable, generally rectangular, cell culture flask having a top wall and a bottom wall connected to side walls and end walls, one of said end walls including a neck and closure, the improvement comprising:

said bottom wall comprising an extended surface area and having an interior surface capable of attachment and confluent growth of animal cells, said bottom wall containing a plurality of parallel, non-horizontal folds and a plurality of flat viewing panels disposed adjacent to said folds and said folds comprising a majority of the interior surface of said bottom wall whereby the surface for cell growth of the bottom wall is significantly increased; and one of said flat viewing panels is disposed adjacent each fold.

15. A cell culture flask, according to claim 14, in which said folds have a longitudinal axis parallel to the side walls.

16. A cell culture flask, according to claim 15, in which said bottom wall has at least about twice the surface area of a comparably sized bottom wall with a flat interior surface.

17. In a stackable, generally rectangular, cell culture flask having a top wall and a bottom wall connected to side walls and end walls, one of said end walls including a neck and closure, the improvement comprising:

said bottom wall comprising an extended surface area and having an interior surface capable of attachment and confluent growth of animal cells, said bottom wall containing a plurality of parallel, non-horizontal folds and a plurality of flat viewing panels disposed adjacent to said folds and said folds comprising a majority of the interior surface of said bottom wall whereby the surface area for cell growth of the following wall is substantially increased;

a plurality of parallel folds being disposed adjacent to each other to form at least one region; and said flat panels completely surrounding each of said regions.

18. A cell culture flask, according to claim, 17 in which said folds have a longitudinal axis parallel to the side walls of the flask.

19. A cell culture flask, according to claim 18, in which said bottom wall has at least about twice the surface area of a comparably sized bottom wall with a flat interior surface.

* * * * *